US006602465B2

(12) United States Patent
Ostby et al.

(10) Patent No.: US 6,602,465 B2
(45) Date of Patent: Aug. 5, 2003

(54) GELATINOUS WOOD PRESERVATIVE

(75) Inventors: David J. Ostby, Madison, WI (US); Michael J. Maloney, Madison, WI (US)

(73) Assignee: S-T-N Holdings, Inc., Las Vegas, NV (US)

( * ) Notice: Subject to any disclaimer, the term of this patent is extended or adjusted under 35 U.S.C. 154(b) by 0 days.

(21) Appl. No.: 09/818,487

(22) Filed: Mar. 27, 2001

(65) Prior Publication Data

US 2002/0172614 A1 Nov. 21, 2002

(51) Int. Cl.[7] .............................. A61L 2/00; A61L 9/00; B01J 19/00

(52) U.S. Cl. ............................... 422/28; 422/1; 422/23; 422/30; 422/37; 422/40; 422/292

(58) Field of Search ...................... 422/528, 32, 36–37, 422/292, 40, 125

(56) References Cited

U.S. PATENT DOCUMENTS 4,738,878 A * 4/1988 Anderson et al.
4,804,398 A * 2/1989 Gehring et al.
4,941,910 A * 7/1990 Muller et al.
5,043,225 A * 8/1991 Ostby et al.
5,236,711 A * 8/1993 Ostby et al.

OTHER PUBLICATIONS

RT&S'a Annual Crosstie Report ; Crosstie Tails; pp. 20–21; Oct. 2000.

* cited by examiner

*Primary Examiner*—Robert J. Warden, Sr.
*Assistant Examiner*—Monzer R. Chorbaji
(74) *Attorney, Agent, or Firm*—Hodgson Russ LLP

(57) ABSTRACT

The general purpose of this invention is to provide an improved apparatus and method of preserving the vulnerable area of a railroad cross tie near the interface of the tie and the tie plate. To attain this purpose the invention provides a thin preservative-bearing gelatinous material that is placed between the cross tie and the tie plate either at the time of the original laying of rail or during any subsequent relaying. No extra equipment is needed and only a negligible amount of labor is required to simply place the gelatinous material on the adzed surface of the cross tie prior to the mounting or remounting of the rail. The presence of the gelatinous material poses absolutely no resistance to the subsequent driving of the spikes into the tie and is thin enough so as not to pose any rail alignment problems. The use of the gelatinous material relies on the moisture found under the tie plate to leach the active ingredients out of the material and help diffuse them throughout the adjacent section of wood. In addition, the unloading and loading of the tie plate by the passing of a train forces moisture into and out of the gelatinous material to further promote the leaching action. The inert components of the gelatinous material are completely biodegradable and will not pose an environmental problem at the end of the material's service life.

8 Claims, 2 Drawing Sheets

GELATINOUS WOOD PRESERVATIVE

FIELD OF THE INVENTION

The present invention relates to a preservative-bearing gelatinous material and method of using same to preserve wooden railroad cross ties.

BACKGROUND OF THE INVENTION

Wooden railroad cross ties are made decay resistant by forcing a material such as creosote into the wood cell structure under relatively high pressure. This protects the exterior wood layer but the interior is not penetrated by the creosote and is subject to attack by decay fungi whenever the exterior layer is split, cracked, abraded away or otherwise structurally compromised. Penetration of the treated exterior is common after extended service use as a result of weathering and also as a result of what is known as spike kill and plate cut.

Weathering typically causes weather checking in the form of splits or cracks running in the direction of the wood grain. These cracks provide passages for moisture to travel under the tie plate supporting the rail and into the tie spike holes and checks.

Spike kill is the mechanical enlargement of spike holes caused by cyclical train loadings on the rail, the spike and the tie plate, the relative movement between these components eventually enlarges the spike hole and exposes the untreated tie wood. This relative movement also causes plate cut, which wears or cuts away the tie at the interface between the tie plate and tie. This action tends to abrade away the treated exterior wood layer and exposes the tie interior to the intrusion of moisture and fungi spores.

Soon after railroad ties are put into service moisture sites become established, particularly in the central portion of the interface between the tie and the tie plate. This central portion never seems to dry. As a consequence, the presence of moisture and the temperature elevation brought on by exposure to the sun serve as an incubator for the growth of decay fungi. The natural balance of food, moisture and temperature accelerates destruction of the wood cells and exaggerates spike kill and plate cut in a cycle which eventually results in premature failure and costly replacement of the ties.

Osmose Incorporated, in U.S. Pat. Nos. 5,236,711 and 5,043,225, disclosed in its summary of the invention "a thin preservative-bearing pad that is placed between the cross tie and the tie plate either at the time of the original laying of rail or during any subsequent relaying." The pad consists of a suspension of a water-soluble fungicide in a binder sandwiched between two layers of a porous hydrophilic backing material. The use of the pad relies on the omni-present moisture found under the tie plate to leach the active ingredients, like sodium fluoride, out of the pad and help diffuse them throughout the adjacent section of wood.

That product, however, has been improved with the present invention because it now does not require a porous hydrophilic backing material and is easier to apply to the wood surface.

SUMMARY OF THE INVENTION

The general purpose of this invention is to provide an improved apparatus and method of preserving the vulnerable area of a railroad cross tie near the interface of the tie and the tie plate. To attain this purpose the invention provides a thin preservative-bearing gelatinous material that is placed between the cross tie and the tie plate either at the time of the original laying of rail or during any subsequent relaying. No extra equipment is needed and only a negligible amount of labor is required to simply place the gelatinous material on the adzed surface of the cross tie prior to the mounting or remounting of the rail. The presence of the gelatinous material poses absolutely no resistance to the subsequent driving of the spikes into the tie and is thin enough so as not to pose any rail alignment problems. The use of the gelatinous material relies on the moisture found under the tie plate to leach the active ingredients out of the material and help diffuse them throughout the adjacent section of wood. In addition, the unloading and loading of the tie plate by the passing of a train forces moisture into and out of the gelatinous material to further promote the leaching action. The inert components of the gelatinous material are completely biodegradable and will not pose an environmental problem at the end of the material's service life.

BRIEF DESCRIPTION OF THE DRAWINGS

Other objects and many of the attendant advantages of this invention will be readily appreciated as the same becomes better understood by reference to the following detailed description when considered in conjunction with the accompanying drawings in which like reference manuals designate like parts throughout the figures thereof and wherein.

DETAILED DESCRIPTION OF A PREFERRED EMBODIMENT

Figure 1:
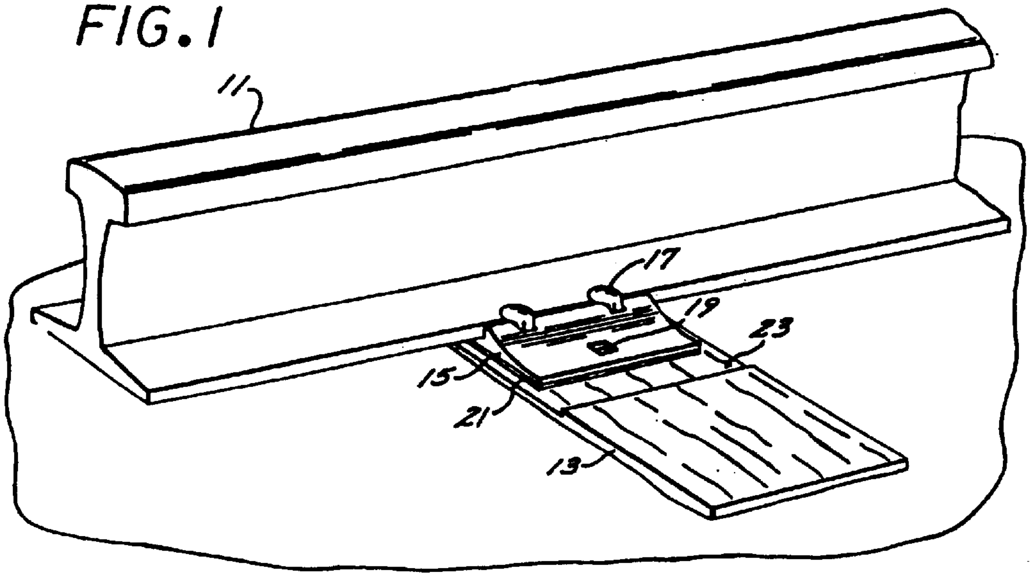
FIG. 1 is a perspective view of the gelatinous material of the present invention in its installed position.
Figure 2:
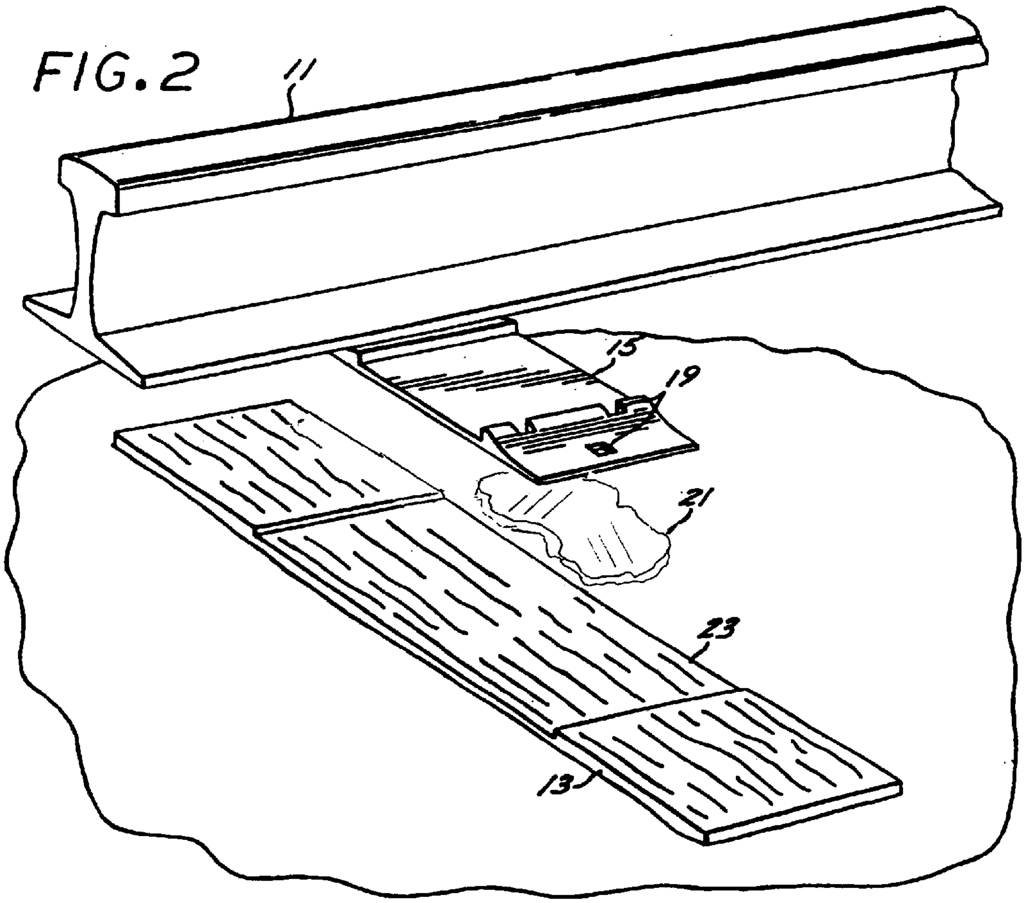
FIG. 2 is an exploded perspective of FIG. 1.
Figure 3:
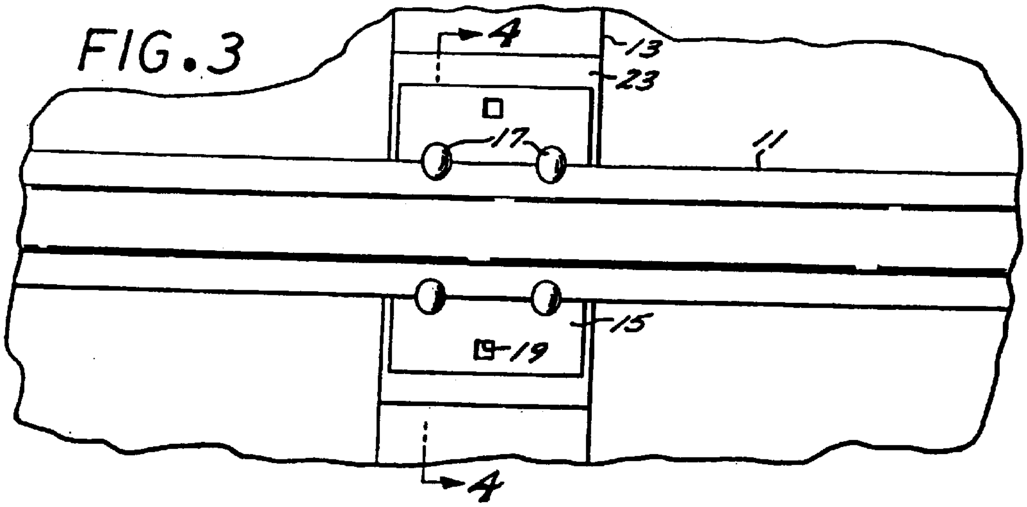
FIG. 3 is a top plan view of FIG. 1.

Reference is made to FIGS. 1–4 which generally illustrate the manner in which a rail 11 is affixed to a cross tie 13 and the placement of the preservative bearing gelatinous material 21 of the present invention. After placement of a tie 13, a section 23 thereof is adzed so as to provide a smooth and level surface for the support of the rail. A tie plate 15, having a plurality of holes 19 therein, is placed on the tie 13 after which the rail is lowered thereon. Conventional practice is to drive spikes 17 through two holes located diagonally on either side of the rail 11. The empty or unoccupied spike holes are available for use in the event that the originally placed spikes 17 become loosened through spike kill. In that event, additional spikes would be driven into originally unoccupied spike holes. The drawing figures illustrate an arrangement employing four spikes, two spikes on either side of the rail, with two extra holes remaining.

The thin preservative bearing gelatinous material 21 of the present invention is placed directly on the adzed surface of the tie 13 prior to placement of the tie plate 15 and subsequently offers no resistance when the spikes 17 are driven into the tie.

The material 21 is a gelatinous composition of a water-soluble active ingredient in a binder and additional agents. Sodium fluoride has been found to be an especially effective fungicide, is water soluble and therefore a preferred active ingredient of the present invention. A matrix of an absorbent polymer with a sodium salt, obtained from Stockhausen Louisiana Limited of Garyville, La. (CAS # 76774-25-9); and offers excellent binding properties, is capable of supporting a substantial amount of sodium fluoride and therefore is well suited as a binder for the present invention. An additional binder, thickener, agent is a cellulose gum product, obtained from the Aqualon division of Hercules Incorporated of Wilmington, Del. (CAS # 9004-32-4). In addition, the material 21 comprises water and an anti-freeze, like propylene glycol. Examples of the materials are shown in Table 1.

TABLE 1

| Component of Material | % of weight percent of Material |
|---|---|
| Water (carrier) | 31.09–29.27 |
| Propylene Glycol (anti-freeze) | 11.62–10.52 |
| Poly (Acrylic Acid), sodium salt, lightly cross-linked (binder) | 1.69–1.53 |
| Sodium Fluoride (active ingredient) | 56.57–53.27 |
| Cellulose Gum (binder) | 0.89–0.73 |

From Table 1, a ratio of sodium fluoride to binder ranges from 56.6:2.6 to 53.3:2.1 by weight (or approximately the ratio of 28:1 to 26.5:1) provides the desired properties for this application. It has been found that an admixture of approximately 56% by weight sodium fluoride and approximately 2.3% by weight binder yields an ideal mass and provides the proper leach rate, given the amount of moisture normally available between the cross tie and tie plate. Unlike the prior embodiment, the material 21 is not limited to a predetermined length and width. Instead, a machine dispenses the material 21 to the adzed surface. Since the material is gelatinous instead of a suspension in a pad, there is a decreased chance of a person readjusting the position of the gelatinous material 21.

Figure 4:
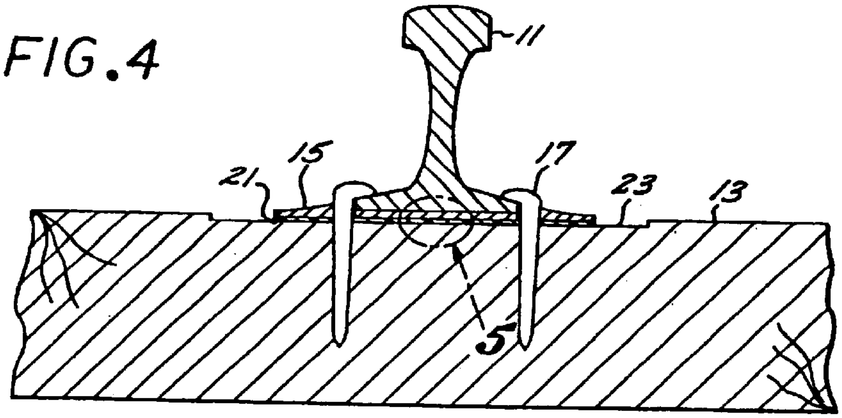
FIG. 4 is a cross-sectional view of FIG. 4, along lines 4—4.
Figure 5:
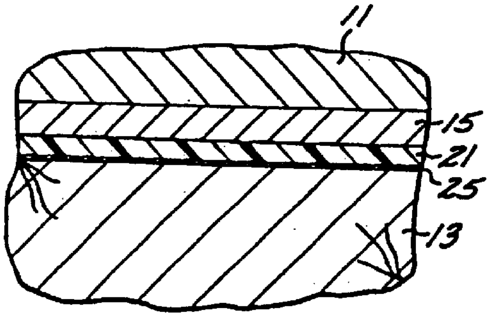
FIGS. 5 and 6 are an enlargement of the circled portion of FIG. 4.
Figure 6:
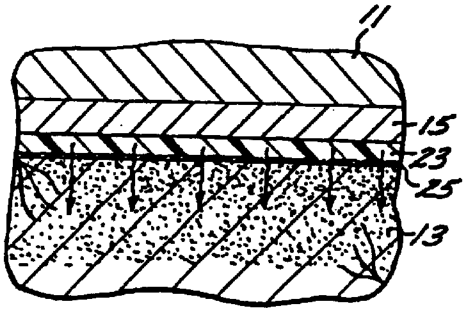

FIGS. 5 and 6 show enlarged cross-sectional views of the encircled area of FIG. 4 and particularly illustrate the positioning of the dispersed material 21. As moisture 25 accumulates between the tie plate 15 and the cross tie 13 it proceeds to seep into the interior of the gelatinous material where it then dissolves sodium fluoride. Once in solution, osmotic pressures will serve to transport (as indicated by the arrows in FIG. 6) sodium fluoride to areas of lesser concentration, i.e., the interior of the wood. As spike holes become enlarged as a result of the spike kill process described above, fungicide-laden moisture has access to even deeper recesses within the wood. The loading and unloading of the rail 11 caused by the passing of a train will serve to pump water into and out of the material thereby expediting the dissipation of fungicide into the cross tie.

It is intended that the gelatinous material of the present invention will be dispensed during the initial laying of the track or during any subsequent relaying operations. After the passage of time, the action of the water underneath the tie plate 15 will serve to transport away the entire mass of active ingredient.

The typical chronology of events depending of course on the actual conditions encountered, is that the sodium fluoride is completely transferred from gelatinous material 21 to the wood within a few months wherein it remains toxicologically active for up to about 5 years. The track is relayed at time intervals anywhere from 5 to 30 years.

Some of the advantages of the gelatinous product over other products are the ease of application, the fact that it is not affected by rail heaters, its cleans up with water, and can be used in any type of weather. Moreover, the machine that applies the gelatinous material, made by Racine Railroad Products of Racine, Wis., can easily dispense the gelatinous material up to 40 ties in a minute.

Various modifications and changes may be made with respect to the foregoing detailed description without departing from the scope of the present invention.

We claim:

1. A method of preserving the wood near the interface of the adzed surface of a wooden railroad cross-tie and a tie plate during a rail laying or re-laying operation, the cross-tie and tie plate being exposed to moisture during railroad operations, said method comprising:

dispensing a gelatinous material comprising a water-soluble fungicide in a binder on the adzed surface, the fungicide leaching from the gelatinous material at a controlled rate when water contacts the gelatinous material, wherein the gelatinous material is biodegradable as the fungicide is leached therefrom;

positioning the tie plate and rail on the adzed surface; and driving the spikes through the tie plates into the cross-tie, with the spikes forming spike holes in the cross-ties whereby the fungicide is transported to the interior of the cross-tie through the spike holes by osmotic pressures and cyclical loading and unloading of the rail caused by the passing of a train expediting dissipation of the fungicide into the cross-tie.

2. A method as set forth in claim 1 wherein the fungicide comprises sodium fluoride.

3. A method as set forth in claim 1 wherein biodegradation of the gelatinous material facilitates replacement of the gelatinous material by a similar gelatinous material during subsequent rail relaying operations.

4. A preservative-bearing gelatinous material for placement between a railroad cross-tie and tie plate comprising:

a gelatinous material of fungicide containing a binder material, the fungicide material selected to be water soluble and the binder material selected to be capable of supporting a substantial amount of the fungicide and operative to allow the fungicide to leach therefrom at a controlled rate when water contacts the gelatinous material;

wherein the gelatinous material is biodegradable as the fungicide is leached therefrom.

5. The gelatinous material of claim 4, wherein the fungicide comprises sodium fluoride.

6. The gelatinous material of claim 5, wherein the binder material comprises an absorbent polymer.

7. The gelatinous material of claim 5 wherein the binder material comprises sodium silicate.

8. The gelatinous material of claim 5 wherein the sodium fluoride and the binder are combined in an approximate ratio of 28:1 to 26.5:1 by weight percent.

* * * * *